(12) United States Patent
Gill et al.

(10) Patent No.: US 7,891,974 B2
(45) Date of Patent: *Feb. 22, 2011

(54) PORTABLE FLUID WARMING SYSTEM

(75) Inventors: Brijesh Gill, Houston, TX (US); Charles Cox, Bellaire, TX (US); Ofodike A. Ezekoye, Austin, TX (US); Ozgur Ekici, Izmir (TR)

(73) Assignee: The Board of Regents of the University of Texas System, Austin, TX (US)

( * ) Notice: Subject to any disclaimer, the term of this patent is extended or adjusted under 35 U.S.C. 154(b) by 820 days.

This patent is subject to a terminal disclaimer.

(21) Appl. No.: 11/832,415

(22) Filed: Aug. 1, 2007

(65) Prior Publication Data

US 2008/0021393 A1  Jan. 24, 2008

Related U.S. Application Data

(63) Continuation-in-part of application No. 10/886,191, filed on Jul. 7, 2004, now Pat. No. 7,261,557.

(51) Int. Cl.
*F23D 14/62* (2006.01)

(52) U.S. Cl. .................. 431/328; 431/326; 431/329

(58) Field of Classification Search ................ 431/268, 431/326, 328, 329; 604/113; 126/208; 607/105
See application file for complete search history.

(56) References Cited

U.S. PATENT DOCUMENTS

| | | | |
|---|---|---|---|
| 1,616,143 A | 1/1927 | Schnepp | |
| 2,904,014 A | 9/1959 | Meyers | |
| 3,590,215 A | 6/1971 | Anderson et al. | |
| 3,808,403 A | 4/1974 | Kanaya et al. | |
| 4,288,346 A | 9/1981 | Hunter et al. | |
| 4,366,804 A | 1/1983 | Abe | |
| 4,464,563 A | 8/1984 | Jewett | |
| 4,480,631 A | 11/1984 | Kristensen | |
| 4,532,414 A | 7/1985 | Shah et al. | |
| 4,716,885 A | 1/1988 | Zaborowski | |
| 4,735,609 A | 4/1988 | Comeau et al. | |
| 4,759,749 A | 7/1988 | Verkaart | |
| 4,878,537 A | 11/1989 | Verkaart | |
| 4,900,308 A | 2/1990 | Verkaart | |
| 5,042,455 A | 8/1991 | Yue et al. | |
| 5,063,994 A | 11/1991 | Verkaart | |

(Continued)

FOREIGN PATENT DOCUMENTS

WO  00 16722  3/2000

(Continued)

OTHER PUBLICATIONS http://www.hypothermia-ca.com; print out, 2 pages.

*Primary Examiner*—Alfred Basichas
(74) *Attorney, Agent, or Firm*—Browning Bushman P.C.

(57) ABSTRACT

The present invention relates to a portable apparatus for warming biocompatible fluids for use in the treatment of injured patients and a method of heating a biocompatible fluid to treat a patient experiencing hypothermia. The present invention may be used to warm intravenous fluids for trauma resuscitation or to warm air from a ventilator circuit. The portable nature of the present invention makes it highly suitable for field applications, such as a forward surgical hospital near a combat zone.

29 Claims, 6 Drawing Sheets

U.S. PATENT DOCUMENTS

| | | |
|---|---|---|
| 5,097,898 A | 3/1992 | Verkaart |
| 5,101,804 A | 4/1992 | Cohn |
| 5,245,693 A | 9/1993 | Ford et al. |
| 5,254,094 A | 10/1993 | Starkey et al. |
| 5,295,964 A | 3/1994 | Gauthier |
| 5,372,709 A | 12/1994 | Hood |
| 5,408,576 A | 4/1995 | Bishop |
| 5,417,274 A | 5/1995 | Verkaart |
| 5,512,043 A | 4/1996 | Verkaart |
| 5,544,645 A | 8/1996 | Armijo et al. |
| 5,807,332 A | 9/1998 | Augustine et al. |
| 5,810,779 A | 9/1998 | Baker et al. |
| 5,930,459 A | 7/1999 | Eckman et al. |
| 6,142,974 A | 11/2000 | Kistner et al. |
| 6,259,067 B1 | 7/2001 | Faries, Jr. et al. |
| 6,294,762 B1 | 9/2001 | Faries, Jr. et al. |
| 6,376,805 B2 | 4/2002 | Faries, Jr. et al. |
| 6,384,380 B1 | 5/2002 | Faries, Jr. et al. |
| 6,608,968 B2 | 8/2003 | Bakke |
| 7,261,557 B2 * | 8/2007 | Gill et al. .................... 431/328 |

FOREIGN PATENT DOCUMENTS

| | | |
|---|---|---|
| WO | 01 62194 A1 | 8/2001 |

* cited by examiner

PORTABLE FLUID WARMING SYSTEM

CROSS REFERENCE TO RELATED APPLICATIONS

This application is a continuation in part of application Ser. No. 10/886,191, filed on Jul. 7, 2004 now U.S. Pat. No. 7,261,557.

BACKGROUND OF THE INVENTION

1. Field of the Invention

The present invention relates to a portable apparatus for warming biocompatible fluids for use in the treatment of injured patients and a method of heating a biocompatible fluid to treat a patient experiencing hypothermia. The present invention may be used to warm intravenous fluids for trauma resuscitation or to warm air from a ventilator circuit. The portable nature of the present invention makes it highly suitable for field applications, such as a forward surgical hospital near a combat zone.

2. Description of the Prior Art

Hypothermia is quite common in injured patients, including patients experiencing trauma. Hypothermia produces a number of physiologic derangements which worsen the effects of major injury. Several relevant enzyme systems begin to lose efficiency as their ambient temperature falls. For example, the myocardium, which is dependent on the function of membrane-channel type enzymes for normal electrical function, shows a predictable series of atrial followed by ventricular arrhythmias as core temperature falls below 34° C. Cardiac output is further compromised by poor function of intrinsic myocardial components, with bovine myocardium showing a linear decrease in developed tension with decreasing temperature.

Hypothermia also exacerbates hemorrhagic shock in multiple ways. The onset of coagulopathy which accompanies hypothermia has been shown to result from malfunction of both clotting factors and platelets.

While profound hypothermia may be tolerated by immersion or cardiac surgery patients, the presence of hypothermia in trauma patients predicts significantly higher mortality. Mortality doubles for heterogeneous groups of trauma patients at 34° C., and survival after trauma is very rare when the core temperature falls below 32° C. This effect is greater for more severely injured patients.

The development of hypothermia comes from several factors. Body heat is convectively lost to the environment, and this effect is enhanced by bleeding or the presence of large surface area burns. The body loses both central thermoregulation and peripheral shivering after traumatic injury. Less heat is produced peripherally as perfusion decreases in shock.

The administration of intravenous fluids is used in trauma resuscitation. The administration of fluid at ambient temperature, however, induces hypothermia. This condition is worse in more severely injured patients, who require the most fluid and have the least ability to tolerate the additional insult of decreased core temperature. Hypothermia and mortality clearly increase after the administration of five liters of crystalloid or five units of packed red blood cells, and the onset of hypothermia increases the incidence of coagulopathy in injured patients, particularly in the presence of acidosis.

As used herein, the term "biocompatible fluid" refers to any fluid that is appropriate for infusion into the human body, including normal saline and its less concentrated derivatives, Ringer's lactate, and hypertonic crystalloid solutions; blood and fractions of blood including plasma, platelets, albumin and cryoprecipitate; intravascular volume expanding blood substitutes including hetastarch, polymerized hemoglobin, perfluorocarbons; medications reconstituted with saline or sterile water; and medical gasses including air, oxygen, helium, nitric oxide, and combinations thereof.

Prior art methods of treating hypothermia include direct intravenous fluid warming. The fluid that is warmed may be blood other biocompatible liquid.

Prior art devices used to warm one or more biocompatible fluids for use in the treatment of trauma have used electricity as their heating source. These systems are referred to herein as "biocompatible liquid infusion systems." Electrically heated biocompatible fluid infusion systems have several drawbacks. If the source of electrical energy is alternating current from a central generating station, the unit can then only be used in locations where such alternating current is available. This significantly limits the locations where the units may be used. Locations such as non-industrialized nations or battlefield locations are likely not to have readily available sources of alternating current to power such systems.

Batteries may also be used to generate electrical energy. It is believed that sufficient power to heat a single liter of fluid to 20° C. within a ten minute time period would require a rechargeable battery the size and weight of a large laptop computer. In such a case, the weight of the battery would exceed the weight of a liter of saline fluid. The size and weight of such a unit would limit its portability. Additionally, the battery would require recharging after each liter of biocompatible fluid is delivered.

The present invention overcomes the limitations of prior art biocompatible fluid infusion systems by providing a biocompatible liquid infusion system that is not dependent upon electrical energy as a heat source. The present invention is light enough and compact enough to be used in field hospital environments which are remotely located from large central hospitals and from sources of alternating current. The present invention may also be used to warm air delivered to a patent via a ventilation circuit.

SUMMARY OF THE INVENTION

Apparatus embodiments of the present invention are directed toward a portable biocompatible fluid warming system that may be used for infusing biocompatible liquids into a patient for the treatment of trauma. Various embodiments of the invention use heat from hydrocarbon combustion. Hydrocarbon combustion can take place in the absence of an open flame. As an example, in one embodiment, the present invention may be used with a gaseous hydrocarbon such as butane which is allowed to flow onto a platinum mesh and then ignited. The butane combines with oxygen and liberates heat which then heats the platinum mesh. In this embodiment, the temperature of the mesh stabilizes at the ignition temperature of the butane, thereby allowing combustion to occur on the surface of the platinum mesh.

Various embodiments of the present invention function as a heat exchanger which takes the heat resulting from the hydrocarbon combustion process described above and transfers this heat to a biocompatible liquid.

Method embodiments of the present invention are directed toward a method of heating a biocompatible fluid to treat a patient experiencing hypothermia.

DESCRIPTION OF THE PREFERRED EMBODIMENTS

Figure 2:
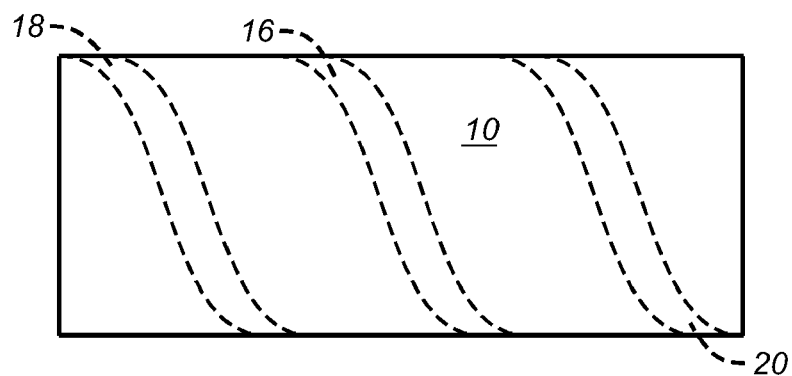
FIG. 2 is a side cutaway view of one embodiment of the present invention.
Figure 3:
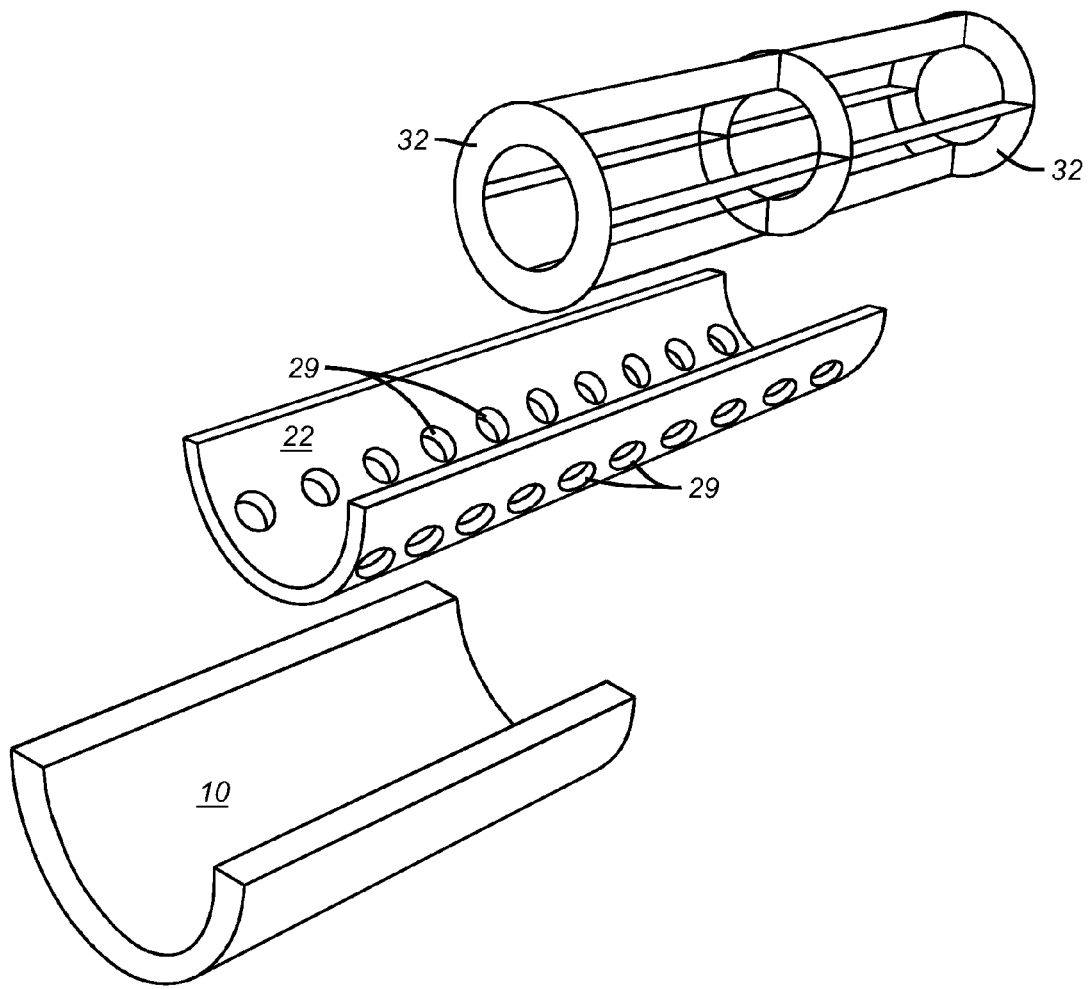
FIG. 3 is an exploded isometric view of one embodiment of the inner housing, the outer housing, and heat transfer protrusions of the present invention.

In a preferred embodiment, the present invention is directed toward a portable warmer of a biocompatible fluid comprising an outer housing 10 comprising a first outer diameter 12, a first inner diameter 14, and at least one flow channel 16 located between the first inner diameter and the first outer diameter as shown in FIGS. 2 and 3. In various preferred embodiments, the outer housing may comprise biocompatible material, including a biocompatible coating. The biocompatible material may be plastic or metal, including stainless steel. The portable warmer is a portable heat exchanger.

The term "diameter" as used herein refers to the length of an axis which bisects a cross sectional area of the housing. For cylindrical geometries the diameter is constant at a given point along the longitudinal axis of the cylindrical housing at various azimuths. For non-cylindrical geometries the diameter at a given point along the longitudinal axis of the housing may vary as a function of the azimuth.

In a preferred embodiment, the outer diameter of the steel housing is no more than 20 centimeters. In another preferred embodiment, the outer housing is cylindrical. In another preferred embodiment, the outer housing is made of stainless steel.

Figure 1:
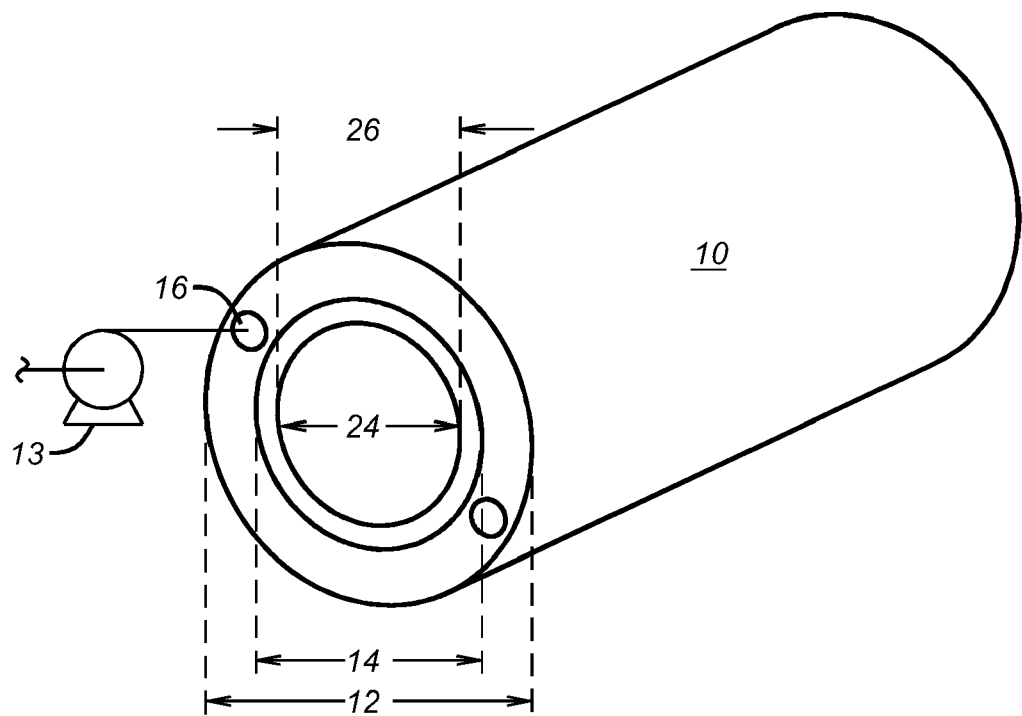
FIG. 1 is an isometric view of one embodiment of the outer housing of the present invention.

The flow channel comprises an inlet section 18 and an outlet section 20, as shown in FIG. 1. In a preferred embodiment, the flow channel is helical, as shown in FIG. 1. In another preferred embodiment, the mass of the portable warmer described herein is less than or equal to two kilograms. In a preferred embodiment, a pump 13 is connected to the inlet section 18, such that it can discharge fluid into the inlet section. The pump comprises a suction inlet and a discharge outlet. In another preferred embodiment, the pump comprises stainless steel or another material suitable for use with a biocompatible fluid. In another preferred embodiment, a reservoir of biocompatible fluid is connected in fluid communication with the suction inlet of the pump. The pump may be a positive displacement or centrifugal pump.

This embodiment of the invention further comprises an inner housing 22 having a second outer diameter 24 sized to fit snugly within said outer housing and an inner wall defining a second inner diameter 26 and an internal volume as shown in FIGS. 2 and 3. The inner housing should be made from a material or materials such that the inner housing will have a specific heat capacity less than or equal to 1000 J/kg °K and a thermal conductivity greater than or equal to 150 W/m °K. In a preferred embodiment, the inner housing is made from aluminum. In the preferred embodiment depicted in FIG. 2, the internal volume defined by inner diameter 26 extends longitudinally the length of outer housing 10. In a preferred embodiment, both the outer and inner housings are cylindrical. In a preferred embodiment, the inner housing comprises at least two ports 29 to permit fluid flow between regions on opposite sides of the inner housing as shown in FIG. 3. In another preferred embodiment, the inner housing comprises at least two grooves in which fluid can flow.

Figure 7A:
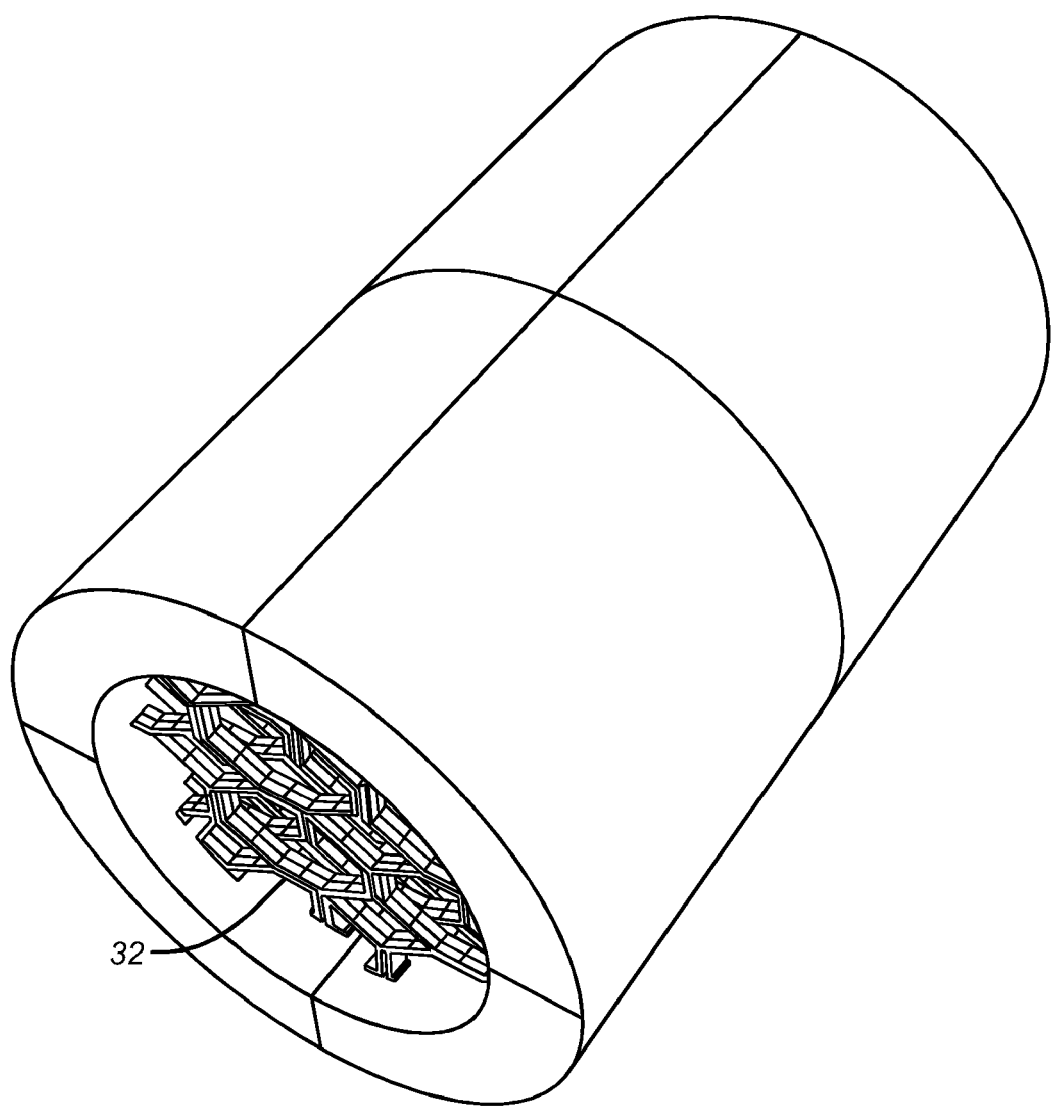
FIG. 7A is an isometric view of a preferred embodiment of heat transfer protrusions for use with an embodiment of the present invention.
Figure 7B:
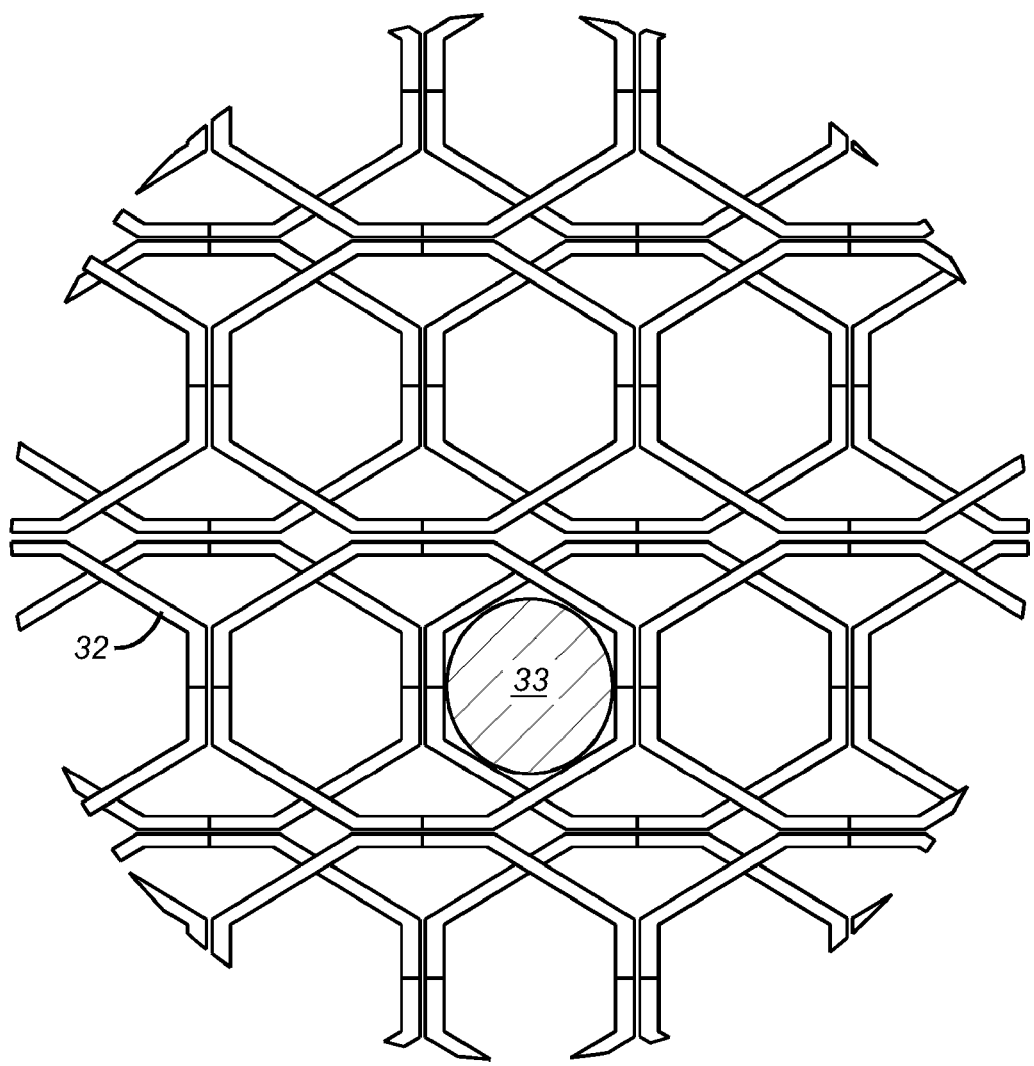
FIG. 7B is an front view of a preferred embodiment of heat transfer protrusions and a heating element for use with an embodiment of the present invention.

This preferred embodiment further comprises a multiplicity of heat transfer protrusions 32 in contact with the inner wall as shown in FIG. 3. In one preferred embodiment, the protrusions are affixed to the inner wall. In another preferred embodiment, the heat transfer protrusions are fins. In another preferred embodiment, the heat transfer protrusions are ring like disks as shown in FIG. 3. In another preferred embodiment, the heat transfer protrusions 32 are a three dimensional lattice or matrix. In another preferred embodiment, the lattice or matrix structure 32 is in the shape of a honeycomb, as shown in FIGS. 7A and 7B. In another preferred embodiment, the honeycomb matrix or lattice is made from aluminum.

Figure 9:
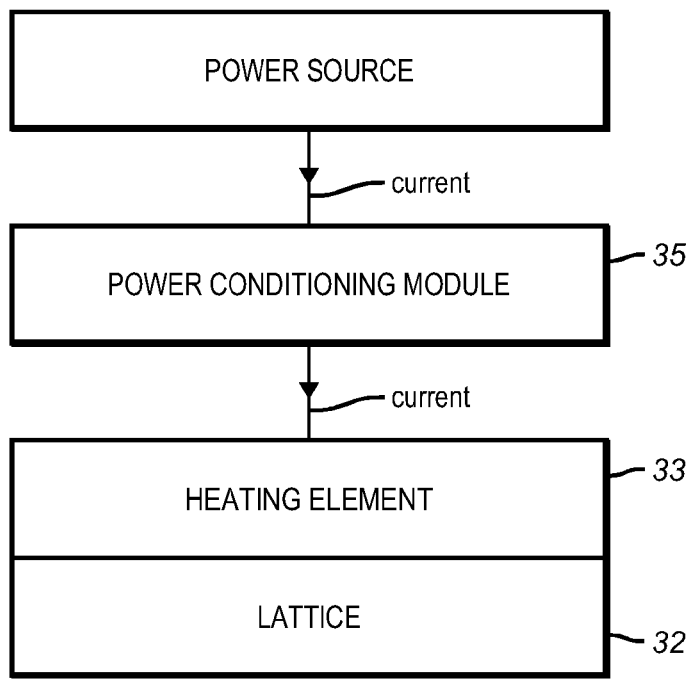
FIG. 9 is a block diagram of the heating element and power conditioning module of an embodiment of the present invention.

In another preferred embodiment, the invention further comprising an electrical heating element 33 in thermal contact with at least one of the heat transfer protrusions, as shown in FIG. 9. In one embodiment the heating element runs on alternating current ("AC"). Such an element is referred to herein as an "AC heating element." In another embodiment, the heating element runs on direct current ("DC"). Such an element is referred to herein as a "DC heating element." In a preferred embodiment, the heating element is waterproof. A suitable waterproof heating element for use in this embodiment of the invention is the Model 288 cartridge heater sold by the George Ulanet Company of Newark, N.J. In another preferred embodiment, the heating element is located coaxially with respect to the lattice or matrix of heat transfer protrusions.

Figure 5:
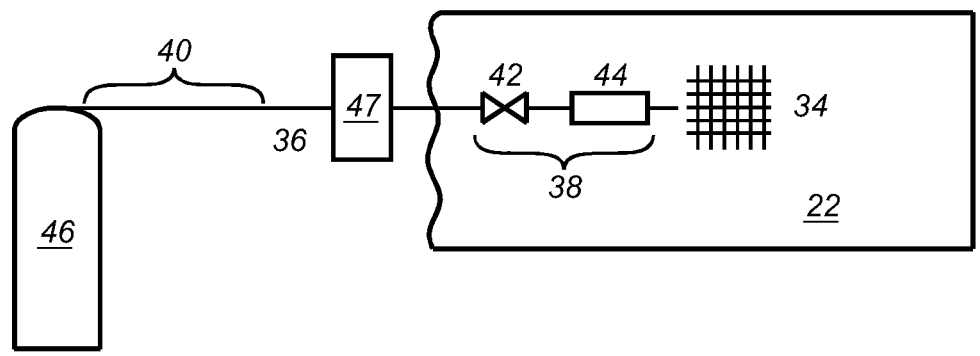
FIG. 5 is a side view of the gas delivery and ignition components of an embodiment of the present invention.

In another preferred embodiment the invention further comprises a power conditioning module 35 operatively coupled to the electrical heating element, as shown in FIG. 9. In a preferred embodiment where the power source is a DC source, and the heating element is an AC heating element, the power conditioning module comprises an inverter that is operatively coupled to receive DC from the power source and to output AC the AC heating element. In a preferred embodiment where the power source is an AC source, and the heating element is a DC heating element, the power conditioning module comprises an AC to DC converter operatively coupled to receive AC from the power source and to output DC to the DC heating element In a preferred embodiment, the invention further comprises a metallic mesh 34 located within the internal cylindrical volume as shown in FIG. 5. In a preferred embodiment, the metallic mesh is made from a metal selected from the group consisting of palladium and platinum. In another preferred embodiment, the metallic mesh comprises a ceramic core coated with platinum.

This invention further comprises a gas delivery line 36 comprising a distal end region 38 located within the internal volume and a proximal end region 40 located outside the internal volume as shown in FIG. 5. A valve 42 is located in the gas delivery line. In a preferred embodiment, the valve is a needle valve. In another preferred embodiment, two or more valves are located in the gas delivery line. In a preferred embodiment, the valve is located in the proximal end region of the gas delivery line.

The invention further comprises an igniter 44 located in the internal volume and situated close enough to the valve such that when the valve is open and gas flows through the gas delivery line and the valve into the internal volume, the igniter can ignite the gas and cause the wire mesh to be heated to a temperature in excess of the ignition temperature of gas selected for use in the gas delivery line. In another preferred embodiment, where the gas selected for use in the gas delivery line is one of butane, propane, or a mixture of butane and propane, the igniter causes the wire mesh to be heated to a temperature in excess of 420° C., as shown in FIG. 5. In a preferred embodiment, the igniter is a spark igniter or a glow plug.

In a preferred embodiment, the invention further comprises a source of combustible gaseous hydrocarbon 46 in fluid communication with the gas delivery line as shown in FIG. 5. In a preferred embodiment, the gaseous hydrocarbon is selected from the group consisting of methane, ethane, propane, and butane. In a preferred embodiment, the source of combustible gaseous hydrocarbon is a fuel tank. In another preferred embodiment, the fuel tank.

In another preferred embodiment, the invention further comprises a fuel air mixer 47 installed in the gas delivery line, as shown in FIG. 5. In a preferred embodiment, the mixer comprises a venturi.

Figure 4:
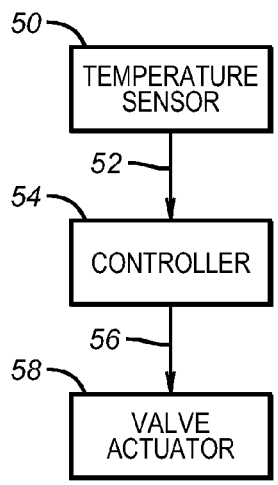
FIG. 4 is a block diagram of the process control instrumentation of a preferred embodiment of the present invention.

Another embodiment of the present invention comprises process controls for controlling the temperature of the fluid output from the portable fluid warmer. In this embodiment, the invention further comprises a temperature sensor 50 positioned to sense the temperature of a fluid flowing through the outlet section of the flow channel and to transmit a temperature signal 52 indicative of the temperature of a fluid flowing through the outlet section of the flow channel as shown in FIG. 4. In a preferred embodiment, the temperature sensor is selected from the group consisting of a thermistor, a thermocouple, and a solid state thermal sensor.

Figure 6:
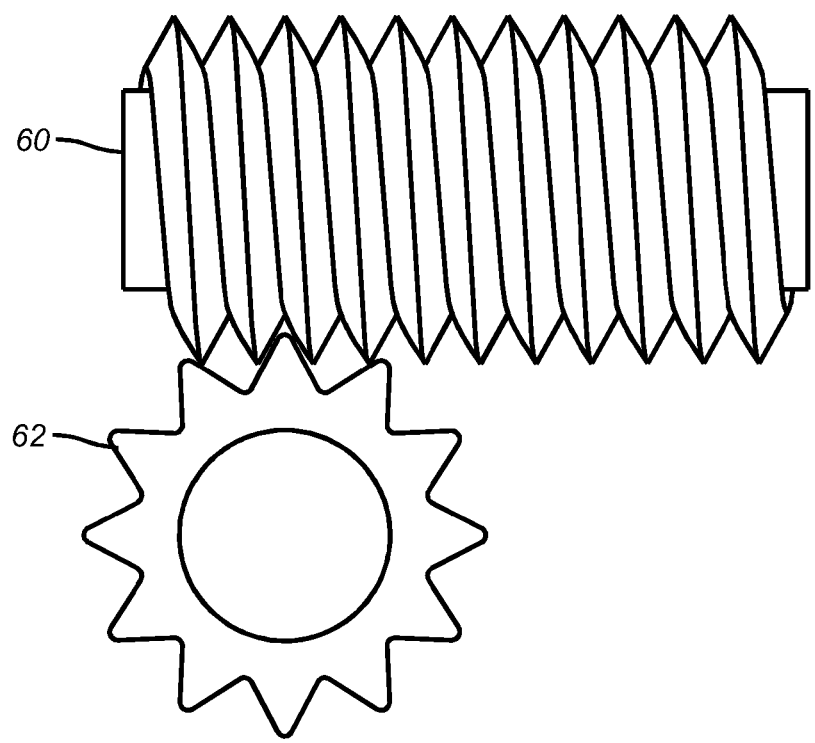
FIG. 6 is a side view of one embodiment of the actuator of an embodiment of the present invention.

In another preferred embodiment, the invention further comprises a controller 54 operatively connected to receive the temperature signal from the sensor and transmit a control signal 56 responsive to the temperature signal as shown in FIG. 4. In one preferred embodiment, the controller is a microcontroller. In another preferred embodiment, the controller is an analog controller. In a preferred embodiment, when the temperature signal indicates that the temperature of the fluid flowing through the outlet section of flow channel exceeds a pre-selected temperature threshold, a control signal to increase the degree of closure of the valve is generated. In another preferred embodiment, the actuator comprises worm gear 60 mechanically coupled to a spur gear 62 as shown in FIG. 6. In this embodiment, the spur gear is mechanically coupled to the valve.

In this embodiment, the invention further comprises a valve actuator 58 operatively connected to the valve and to the controller to control the degree of closure of the valve in response to the control signal as shown in FIG. 4. In a preferred embodiment, the valve actuator is coupled to receive the control signal from the controller. In a preferred embodiment, the valve actuator is a solenoid. In another preferred embodiment, the valve actuator is one or more solenoids. In this embodiment, each valve has an exit orifice. In this embodiment, each exit orifice is sized to provide a specific gas flow rate.

In other embodiments, temperature may be regulated by controlling fuel flow into the inner cylinder. Additionally, temperature may be controlled by mixing small amounts of unheated fluid with the heated fluid exiting the portable warming device. In another embodiment, fluid temperature may be controlled by changing the thermal conductance of the layer between the inner cylinder and the flow channels.

Figure 8:
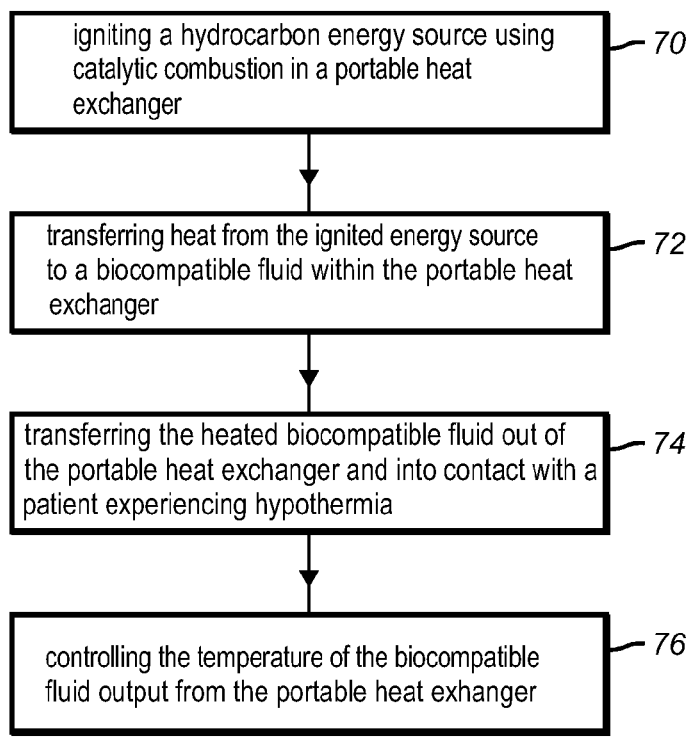
FIG. 8 is a block diagram of a method embodiment of the present invention.

A method embodiment of the invention comprises igniting a hydrocarbon energy source using catalytic combustion in a portable heat exchanger, as shown in block 70 of FIG. 8. In preferred embodiments, the igniting is performed using a glow plug or a spark igniter.

A method embodiment of the invention further comprises transferring heat from the ignited energy source to a biocompatible fluid within the portable heat exchanger, as shown in block 72 of FIG. 8. In a preferred embodiment, the transferring is performed by causing gaseous hydrocarbon to flow through one region of a heat exchanger while a biocompatible fluid flows through another regions of the heat exchanger.

A method embodiment of the invention further comprises transporting the heated biocompatible fluid out of the portable heat exchanger and into contact with a patient experiencing hypothermia, as shown in block 74 of FIG. 8.

Another method embodiment further comprises controlling the temperature of the biocompatible fluid output from the portable heat exchanger, as shown in block 76 of FIG. 8. In one preferred embodiment, the controlling comprises controlling the flow rate of biocompatible fluid through the portable heat exchanger. In another preferred embodiment, the controlling comprises controlling the flow rate of gaseous hydrocarbon through the portable heat exchanger.

The foregoing disclosure and description of the invention are illustrative and explanatory. Various changes in the size, shape, and materials, as well as in the details of the illustrative construction, may be made without departing from the spirit of the invention.

What is claimed is:

1. A portable warmer of a biocompatible fluid comprising:
    (a) an outer housing comprising a first outer diameter, a first inner diameter, and at least one flow channel located between said first inner diameter and said first outer diameter, said flow channel comprising an inlet section and an outlet section;
    (b) an inner housing having a second outer diameter sized to fit snugly within said outer housing and an inner wall defining a second inner diameter and an internal volume, said inner housing having a specific heat capacity less than or equal to 1000 J/kg ° K and a thermal conductivity greater than or equal to 150 W/m ° K;
    (c) a multiplicity of heat transfer protrusions in contact with said inner wall;
    (d) a metallic mesh located within said internal cylindrical volume;
    (e) a gas delivery line comprising a distal end region located within said internal volume and a proximal end region located outside said internal volume;
    (f) a valve located in the gas delivery line; and
    (g) an igniter located in said internal volume and situated close enough to said valve such that when said valve is open and gas flows through said gas delivery line and said valve into said internal volume, the igniter can ignite the gas and cause the wire mesh to be heated to a temperature in excess of the ignition temperature of gas selected for use in the gas delivery line.

2. The device of claim 1, wherein the metallic mesh is made from a metal selected from the group consisting of palladium and platinum.

3. The device of claim 1, wherein the metallic mesh comprises a ceramic core coated with platinum.

4. The device of claim 1, wherein the igniter is a glow plug.

5. The device of claim 1, wherein said flow channel is helical.

6. The device of claim 1, wherein the mass of the portable warmer is less than or equal to 2 kilograms.

7. The device of claim 1, wherein the outer diameter of the housing is no more than 20 centimeters.

8. The device of claim 1, wherein said heat transfer protrusions are disc like rings.

9. The device of claim 1, wherein said heat transfer protrusions are a three dimensional matrix.

10. The device of claim 9, wherein said matrix is in the shape of a honeycomb.

11. The device of claim 10, wherein said honeycomb matrix comprises aluminum.

12. The device of claim 1, further comprising a source of combustible gaseous hydrocarbon in fluid communication with the gas delivery line.

13. The device of claim 12, wherein said gaseous hydrocarbon is selected from the group consisting of methane, ethane, propane, and butane.

14. The device of claim 12, further comprising a fuel air mixer installed between the source of combustible gaseous hydrocarbon and the gas delivery line.

15. The device of claim 1, wherein the outer housing comprises a biocompatible material.

16. The device of claim 1, wherein the inner housing comprises aluminum.

17. The device of claim 1, further comprising:
 (a) a temperature sensor positioned to sense the temperature of a fluid flowing through the outlet section of said flow channel and to transmit a temperature signal indicative of the temperature of a fluid flowing through the outlet section of said flow channel;
 (b) a controller operatively connected to receive said temperature signal from said sensor and to transmit a control signal responsive to said temperature signal; and
 (c) a valve actuator operatively connected to said valve and to said controller to control the degree of closure of said valve in response to said control signal.

18. The device of claim 17, wherein said temperature sensor is selected from the group consisting of a thermistor, a thermocouple and a solid state thermal sensor.

19. The device of claim 17 wherein a control signal to increase the degree of closure of said valve is generated when the temperature signal indicates that the temperature of said fluid flowing through the outlet section of said flow channel exceeds a pre-selected temperature threshold.

20. The device of claim 19, wherein the controller is a microcontroller and the valve actuator is a servo-controller.

21. The device of claim 17, wherein the controller is an analog controller.

22. The device of claim 17, wherein said actuator comprises a solenoid.

23. The device of claim 1, wherein said inner housing comprises at least two ports to permit fluid flow between regions on opposite sides of said inner cylinder.

24. The device of claim 1, wherein said inner housing comprises at least two grooves in which fluid can flow.

25. The device of claim 1, further comprising:
 (a) an electrical heating element in thermal contact with at least one of the heat transfer protrusions; and
 (b) a power conditioning module operatively coupled to the electrical heating element.

26. The device of claim 25, wherein the heating element is waterproof.

27. A portable warmer of a biocompatible fluid comprising:
 (a) an outer housing comprising a first outer diameter, a first inner diameter, and at least one flow channel located between said first inner diameter and said first outer diameter, said flow channel comprising an inlet section and an outlet section;
 (b) an inner housing having a second outer diameter sized to fit snugly within said outer housing and an inner wall defining a second inner diameter and an internal volume, said inner housing having a specific heat capacity less than or equal to 1000 J/kg ° K and a thermal conductivity greater than or equal to 150 W/m ° K;
 (c) a multiplicity of heat transfer protrusions in contact with said inner wall;
 (d) a metallic mesh located within said internal cylindrical volume;
 (e) a gas delivery line comprising a distal end region located within said internal volume and a proximal end region located outside said internal volume;
 (f) a valve located in the gas delivery line;
 (g) an igniter located in said internal volume and situated close enough to said valve such that when said valve is open and gas flows through said gas delivery line and said valve into said internal volume, the igniter can ignite the gas and cause the wire mesh to be heated to a temperature in excess of the ignition temperature of gas selected for use in the gas delivery line; and
 (h) a pump connected to the inlet section, such that it can discharge fluid into the inlet section.

28. The device of claim 27, wherein the pump comprises stainless steel.

29. The device of claim 27, further comprising:
 (a) an electrical heating element in thermal contact with at least one of the heat transfer protrusions; and
 (b) a power conditioning module operatively coupled to the electrical heating element.

* * * * *